United States Patent [19]

Clark

[11] Patent Number: 4,847,083
[45] Date of Patent: Jul. 11, 1989

[54] TWO-STEP PROCEDURE FOR INDOLENT WOUND HEALING AND AQUEOUS MEDIUM AND TOPICAL OINTMENT USED IN CONNECTION THEREWITH

[75] Inventor: Mary G. Clark, Old Forge, Pa.

[73] Assignee: Dermasciences, Inc., Old Forge, Pa.

[21] Appl. No.: 19,768

[22] Filed: Feb. 27, 1987

Related U.S. Application Data

[63] Continuation-in-part of Ser. No. 847,234, Apr. 2, 1986, abandoned.

[51] Int. Cl.$^4$ .............................................. A61K 33/24
[52] U.S. Cl. ..................................... 424/642; 424/680; 424/687; 424/690; 424/692; 514/159; 514/494; 514/561
[58] Field of Search ............... 514/451, 494; 424/145, 424/154, 156, 157

[56] References Cited

U.S. PATENT DOCUMENTS

| | | | |
|---|---|---|---|
| 209,331 | 10/1878 | Daniel | 424/145 |
| 1,411,577 | 4/1922 | Mullins et al. | 424/145 |
| 2,556,567 | 6/1951 | Wright et al. | 424/145 |
| 2,846,349 | 8/1958 | Erskin et al. | 424/146 |
| 3,418,416 | 12/1968 | Fourneau | 424/263 |
| 3,784,685 | 1/1974 | Kalopissis et al. | 424/70 |
| 3,856,941 | 12/1974 | Turner | 424/145 |
| 3,859,436 | 1/1975 | Jacobi | 424/180 |
| 3,887,704 | 6/1975 | Lichtenstein | 424/145 |
| 4,005,191 | 1/1977 | Clark | 424/154 |
| 4,160,821 | 7/1979 | Sipos | 424/49 |
| 4,252,796 | 2/1981 | Yu et al. | 424/179 |
| 4,309,411 | 1/1982 | Toida et al. | 424/63 |
| 4,372,296 | 2/1983 | Fahim | 424/166 |
| 4,401,651 | 8/1983 | Knutson | 424/80 |
| 4,406,881 | 9/1983 | Ladanyi | 424/49 |
| 4,503,037 | 3/1985 | Szijjarto et al. | 424/94 |
| 4,550,022 | 10/1985 | Garabedian et al. | 424/127 |
| 4,564,522 | 1/1986 | Rocke | 424/195 |

OTHER PUBLICATIONS

Hubert E. Buffum, M.D. et al., The Household Physician, 1923, pp. 630, 631, 1063.
Albert L. Lehninger, Biochemistry, 1975, pp. 45–53, 71–72, 77–80, 90, 91, 334, 345, 481–485 and 1047–1048.

Primary Examiner—Leonard Schenkman
Attorney, Agent, or Firm—Staas & Halsey

[57] ABSTRACT

Decubitus ulcers are treated with a preconditioning aqueous medium and then with a non-systemic basic ointment. The aqueous medium comprises an aqueous solution of pyridoxine hydrochloride, zinc chloride, dextrose, ethanol and sodium chloride, with a trace of phenyl mercuric nitrate N.F., and has a pH in the range of 4.3 to 6.8 so as to facilitate ionization of naturally occurring amino acids at the wound site. The ointment comprises calcium carbonate, magnesium hydroxide, aluminum hydroxide, zinc chloride, sodium chloride, anhydrous lanolin, hydrophilic ointment and vitamin A and has a pH in the range of from about 6.5 to 9.0 so as to facilitate chelation of the amino acid and zinc ions and enhance tissue repair.

38 Claims, No Drawings

TWO-STEP PROCEDURE FOR INDOLENT WOUND HEALING AND AQUEOUS MEDIUM AND TOPICAL OINTMENT USED IN CONNECTION THEREWITH

FIELD OF THE INVENTION

The present invention relates to the treatment of injured mammalian tissue, for example, abraded, lacerated or ulcerated tissue, and particularly to such treatment which involves application of a topical ointment to the injured tissue. More specifically, the present invention relates to a two-step treatment with a preconditioning aqueous medium and a topical ointment and to the medium and ointment for such treatment.

DESCRIPTION OF THE PRIOR ART

Pressure wounds or sores called "bedsores" by the laity and decubitus ulcer disease by the medical professional, involve one of the most costly and dreaded skin conditions affecting particularly elderly geriatric patients. Such sores or ulcers are chronic, morbid conditions of the skin commonly found among the disabled, elderly and bedridden population of hospitals and nursing homes. It is estimated that one out of three people 65 years of age or older suffer or have suffered from this dreaded affliction. As predicted by the U.S. Census Bureau, by the year 2010 there will be over 65 million people in the United States in this geriatric age group. Not only does the affliction present a problem to the patient, but also to the institution caring for such individuals. The tremendous cost to the state and federal government to cover the cost of caring for such wounds is staggering. It is estimated by recent reports summing up patient care hours for diagnostic related groupings, that the cost of pressure sore treatment amounts to as much as $62,500.00 per patient annually. This is indeed draining to the institutional health care budget.

Bedsores are often under treatment for months and sometimes even years with daily application of generally ineffective anecdotal therapies. Such anecdotal therapies range from mechanical devices such as cotton filled doughnuts, air filled mattresses, rotating beds, Clinitron beds, foam mattresses and air suspension mattresses, to a variety of topical preparations which are applied locally to the wound area including "debriders" or enzyme preparations to eat away the dead cells so that the living cells may survive, topical antibiotics to treat infections of the area, betadine washes, normal saline rinses, hydrogen peroxide soaks, wet to dry dressings, debrisan, duoderm, occlusive dressings, silvadine ointments, elase ointments and travase ointment. And the list goes on and on.

The present applicant is also the inventor of the subject matter for which U.S. Pat. No. 4,005,191 was granted on Jan. 5, 1977. The ointment and treatment set forth in the '191 patent were discovered serendipitously in about 1972 when the ointment was used to treat a female, diabetic patient suffering two large bedsores, of the right and left gluteous maximus muscles respectively. The wounds were 12 cm. deep, conical in shape, and oozing sero-sanguinous drainage with a foul smelling gas being emitted from each ulcer crater. Dark greenish black eschar clung to the edges of the craters. The patient was scheduled for reconstructive surgery at this time. The '191 ointment was applied to this decaying flesh every 12 hours and a dramatic change took place within three days after application was begun. The area that once was oozing sero-sangunious drainage has cleared and the foul smelling gas had disappeared and instead of a dark green eschar adhering to the area, pink tissue was seen for the first time since the onset of the problem. Continuous treatment was done by the patient's husband, with bi-weekly visits by a registered nurse clinician. The ulcers continued to heal with dramatic rapidity until both craters were closed. The healing took place from the bottom to the top of the crater producing a half moon crescent scar on each gluteous maximus muscle. This patient is still living in a small town in Northeastern Pennsylvania. Since that time, many wounds have responded to such treatment.

The present invention provides improvements over the materials and procedures disclosed and claimed in U.S. Pat. No. 4,005,191. The ointment claimed in said prior patent has been generally effective; however, in some cases, due to the complexities of the human physiology, healing would occur slowly. In some cases, healing would progress swiftly at first but would slow noticeably later on during the healing process. In a few isolated instances, sloughing and/or tunneling of tissue was encountered and treatment was discontinued. Such difficulties often, but not exclusively, have occurred in connection with patients having conditions involving extensive soft tissue chemistry impairment stemming from Paget's disease, metastatic carcinoma of the bone, kidney or lung, elevated SGOT and SGPT, or severe iron difficiency anemia.

Indolent wounds where healing either fails to take place completely, or starts and subsequently fails to progress, present major problems, especially in elderly patients, and/or particularly over boney prominences. However, it has been discovered in accordance with the present invention, that the most common cause of non-healing wounds is probably the initial biochemical condition of the environment of the wound site itself.

The wound site environment changes from one patient to another and in a number of different ways. Inflammation brings in large numbers of phagocytes and growth factors including the metabolic materials required for repair of tissues. Accordingly, such aggravations tend to produce hypoxia due to increases in oxygen uptake. Since much of the energy produced is glycolytic, phagocytes tend to reduce the local pH, especially through the production of lactic acid. This is in itself beneficial, in that lactate is bacteriostatic and also stimulates the formation of collagen. However, in many wounds which are slow to heal or are non-healing, lactic acid production may become excessive, causing the area pH to drop to a very low level, thus causing damage to surrounding cells. The center of such wounds is almost always anoxic, with a pH of approximately 3. If such an environment is not changed, the wounds simply continue to degenerate and decay. Moreover, such acidic pH levels preclude the presence in the wound area of effective levels of basic amino acids, such as lysine, which are needed for proper regeneration of tissue.

In the typical bedsore ulcer, there is a rim of inflamed tissue which is closely adjacent to fibrosed scar and covered only by an exudate of inflammatory cells or a layer of inactive granulation tissue. The blood supply is poor, and the oxygen tension at the growing surface is low. The exudate is generally rich in proteolytic enzymes and harbours low grade bacterial infection. As a result, there is a slow epidermal migration and what few cells are produced are cast adrift after they have moved out onto the surface of any granulation tissues that may be present.

In some ulcers, the oxygen tension is extremely high and a scarcity of macrophages has been noted. When this occurs there is no stimulus to angiogenses, since it has been shown that hypoxic macrophages produce angiogenic factors. From recent research, it would appear that there is something in the environment of particularly bedsore ulcers which prevents either such priming from being successful or the results of activation from acting on other cells. In accordance with the present invention this is believed to be due to the low pH.

In retrospect, the many thousands of patients suffering indolent wounds present a variety of complexities which may be considered. On the other hand, and in accordance with the present invention, the one factor of primary importance in the care of this type of wound is that the biochemical environment of the wound site, and particularly the pH thereof, must be adjusted at the time of treatment. The balance in body chemistry with respect to hydrogen and hydroxyl ions is essential for life to exist. Therefore, it is through the mechanism of the present invention, including a two-step procedure for treating wounds with an aqueous moisturizer media having a pH of from about 4.8 to 6.8 and then with an inorganic non-systemic basic ointment having a pH of from about 6.5 to 9.0, that the environment of the site of indolent wounds may be modified and stabilized to thus create an environment conducive to healing and providing basic amino acids in a form which facilitates tissue growth.

While it is unquestionably known that the carboxyl groups of amino acids undergo disassociation at basic pH levels and that amino acids have buffering capacities in the pH zones near their pK' values, i.e., pH 1.3 to 3.3 and 8.6 to 10.6, it has not been known prior to the present invention that both acidic and basic conditions can be created at essentially the same time in the same wound site to first transport basic amino acids, such as lysine, out of the body tissue and into aqueous solution at the wound site surface by ionizing the carboxyl groups of the amino acids at acidic pH levels, and then causing the basic amino acids to undergo chelation with a chelating agent at basic, or at least higher, pH levels. Manifestly, such procedure is useful in accordance with the invention to facilitate the availability of basic amino acids, such as lysine, at the wound site and to thus enhance tissue growth and regeneration.

SUMMARY OF THE INVENTION

The principal objective of the present invention is to minimize or eliminate the problems outlined above by providing an improved basic ointment, an improved aqueous medium to facilitate availability of basic amino acids and an improved two-step treatment procedure which includes the preliminary application of the novel moisturizing medium for stabilizing the wound site and providing an aqueous environment wherein the pH level is sufficiently high to cause at least partial ionization of basic amino acids and bring such amino acids into aqueous solution at the surface of the wound prior to the application of the ointment. The ointment, which is applied to the treated wound area, is at a pH level sufficient for activation of the amino acids at the surface of the wound. Through the use of the invention, injured tissues may be healed more effectively and efficiently in a greater number of patients.

It is another object of the invention to provide a topical ointment composition useful for treating injuries to the skin which result in ulcerated, lacerated and abraded tissue.

It is a further object of the present invention to provide a filling or cementing material for injured tissue which is soft, flexible, protective and non-irritating and which provides a temporary nucleus to facilitate the growth of replacement tissues for healing purposes.

Another important object of the invention is to provide a moisturizing composition effective for stabilizing and preconditioning the wound area to thereby facilitate the action of the ointment.

Briefly, the compositions and procedures of the instant invention are useful in treating various injuries to the skin which result in ulcerated, lacerated or abraded tissue. In particular the invention facilitates the treatment of decubitus ulcers. Even more particularly the invention provides a method for treating open wounds and human tissue which comprises treating the wound area with an aqueous medium having a pH sufficiently high to cause at least partial ionization of basic amino acids naturally present in tissues adjacent the wound area and bring such basic amino acids into solution at the surface of the wound area, and thereafter treating the wound area with a basic ointment material having a pH level sufficient for activating the basic amino acids at the surface of the wound. In a preferred form of the method of the invention, the pH of the medium is in the range from about 4.3 to 6.8, and in its particularly preferred form, the invention involves the use of a medium wherein the pH is about 5.5 to 5.8. The aqueous medium may contain a chelating agent for the basic amino acids and the chelating agent preferably comprises zinc ions. In this regard, the medium may contain both zinc and chloride ions.

In another particularly preferred form of the invention, the pH of the ointment material may be in the range of from about 6.5 to about 9.0 and in the most preferred form of the invention, the pH of the ointment will be about 8.5. The ointment material may comprise a non-systemic basic material and in a preferred form may include magnesium hydroxide. In this latter regard, the particularly preferred ointment comprises a mixture of magnesium hydroxide aluminum hydroxide and calcium carbonate. The ointment may also include an ionizable zinc salt and the pH of the ointment may then be manipulated to achieve the desired pH level by adjusting the concentration of the zinc salt in the ointment. The respective pH levels of the aqueous medium and of the ointment are preferably selected such that normal pH of healthy tissue of the type being treated is approximately at the median of such levels.

The invention particularly provides a method for treating open wounds in human tissue comprising treating the wound area with an aqueous medium containing a chelating agent for amino acids and having a pH in the range from about 4.3 to 6.8, and thereafter applying, to the treated wound area, an ointment material containing a non-systemic basic material and having a pH in the range from about 6.5 to 9.0. The pH levels of the medium and the ointment are such that the normal pH of healthy tissue of the type being treated is approximately at the median of the levels. In this latter regard, the method may be used for treating open wounds in human dermal tissue, and in such application the pH levels of the median and the ointment should be selected such that the medium of these levels will be in the range of approximately 6.75 to 7.45. The method may also be used for treating open wounds in human epidermal tissue and in this application the pH levels of the medium and the ointment will be selected such that the median of such levels is in the range of approximately 6.0 to 6.4 and most preferably will be about 6.1.

In another aspect, the invention provides materials for treating open wounds in human tissue comprising an aqueous medium for initially treating the wound area, such medium containing a chelating agent for amino acids and having a pH in the range from about 4.3 to 6.8, and a topical ointment for application to the treated wound area, such ointment containing a non-systemic basic component and having a pH in the range from about 6.5 to 9.0. The chelating agent may comprise zinc ions and the medium may also include anions selected from the group consisting of chlorides, sulfates, perioxidases, citrates, acetates and salicylates. The medium may also include a physiologically active amount of a vitamin $B_6$ compound, chloride ions, corn syrup, sodium ions, ethanol and phenylmercuric nitrate. The medium may comprise a sufficient amount of zinc ions to establish a preselected pH in the medium and thereby activate basic amino acids at the surface of an open wound treated with the medium. The topical ointment may comprise an admixture of the basic component, anhydrous lanolin, hydrophilic ointment and a water soluble zinc salt. The ointment may also contain anhydrous lanolin and hydrophilic ointment in amounts effective to carry the other ingredients, facilitate application of the other ingredients to the wound and maintain such other ingredients in wound healing proximity to the wound.

The invention also provides a procedure for treating open wounds in human skin comprising stabilizing and preconditioning such wound by moistening the same and adjusting the pH thereof to a level for causing naturally occurring amino acids to be present at the surface of the wound area, and thereafter covering the moisturized wound with a topical ointment comprising a non-systemic basic component. The ointment should have a pH level sufficient to activate the amino acids. The novel liquid moisturizing composition provided by the present invention is useful for treating open wounds in human skin and comprises an aqueous solution containing a chelating agent for amino acids and should have a pH in the range of from about 4.3 to 6.8, effective upon application to the wound area to stabilize and precondition the open wound and create at the surface thereof an aqueous physiological environment conducive to healing of the wound and containing ionized basic amino acids. The chelating agent may comprise a water-soluble zinc salt, present in an amount physiologically effective to enhance wound healing. The solution may also include a physiologically active amount of a vitamine $B_6$ compound.

The invention also provides a novel topical ointment composition comprising an admixture of a non-systemic basic material, anhydrous lanolin, a hydrophilic ointment and a water-soluble zinc salt. The basic material in the ointment includes calcium carbonate, magnesium hydroxide and aluminum hydroxide in amounts effective for promoting growth of normal healthy body tissues, the zinc salt is included in an amount physiologically effective to enhance wound healing and provide a pH level within the range of from about 6.5 to about 9.0 and the anhydrous lanolin and the hydrophilic ointment are present in amounts effective for carrying the other ingredients, facilitating application of the ingredients to the wound area and maintaining the same in wound healing proximity to the wound.

Other objects and advantages of the present invention including stability, convenience, economy and adaptability for use in conjunction with various known materials will be apparent from the following detailed description of the preferred embodiments thereof.

DETAILED DESCRIPTION OF THE INVENTION

A detailed description of the structure and function of human skin, supporting tissues, connective tissues and viscera, and the nature and sources of injuries thereto, is provided in said U.S. Pat. No. 4,005,191, the entirety of the disclosure of which is specifically incorporated herein by reference. Also disclosed in the '191 patent are a variety of prior art compositions useful for treatment of injuries to the skin. The entirety of the disclosure of co-pending patent application Ser. No. 847,234 is also specifically incorporated herein by reference.

In accordance with the certain aspects of the present invention, a preconditioning or moisturizing composition is applied to the wound to stabilize the same and adjust the pH, thereof, and thereafter an ointment is applied to the stabilized area to again adjust the pH and facilitate desirable chemical interactions. It is theorized, in accordance with the present invention, that through the application of the moisturizer at an acidic pH and then application of a non-systemic basic ointment at a higher pH, the entire nature of the wound area may be transformed and adapted to provide the ingredients and conditions conducive to wound healing.

In a useful embodiment of the improved ointment composition of the present invention, an admixture is provided which comprises a non-systemic basic material, anhydrous lanolin, a hydrophilic ointment and a water-soluble zinc salt. The non-systemic material includes calcium carbonate, magnesium hydroxide and aluminum hydroxide in amounts effective for promoting growth of normal healthy tissues. The zinc salt may be present in an amount physiologically effective to adjust the overall pH of the ointment and enhance wound healing. The anhydrous lanolin and hydrophilic ointment may be present in amounts effective for carrying the other ingredients, facilitating application of the ingredients to the wound area and maintaining the ingredients in wound healing proximity to the wound. The non-systemic basic material preferably comprises from about 7 to about 82 weight percent calcium carbonate, from about 5 to about 77 weight percent magnesium hydroxide and from about 6 to about 80 weight percent aluminum hydroxide and the percentages of such components in the basic material generally total approximately 100 percent thereof. A sufficient amount of water may be added to the non-systemic material to provide a smooth, moist paste. The anhydrous lanolin and the hydrophilic ointment, which together present the carrier material, may be admixed in a weight ratio ranging from approximately 2:1 to approximately 1:2 and the non-systemic basic material may be blended with the admixture of carrier materials. The amount of zinc salt in the admixture may be sufficient to adjust the pH of the admixture to 6.5 to 9.0. Generally, the weight ratio of carrier materials to non-systemic basic material in said composition may usefully be in the range of from about 21:1 to about 213:1.

The basic material may contain from about 25 to about 50 weight percent of each of the enumerated compounds and the composition may contain substantially equal quantities of the carrier materials. In a particular useful form, the topical ointment composition may contain the following ingredients in the indicated proportions:

| INGREDIENT | QUANTITY |
|---|---|
| calcium carbonate U.S.P. | 250 mg |
| magnesium hydroxide U.S.P. | 200 mg |
| aluminum hydroxide U.S.P. | 225 mg |
| zinc chloride U.S.P. | 15 mg |
| sodium chloride U.S.P. | 2.5 mg |
| anhydrous lanolin U.S.P. | 41.29 gm |
| hydophilic ointment U.S.P. | 34 gm |
| vitamin A U.S.P. | 5000 IU |
| water | 24.02 gm |

In mixing the above ingredients to yield a topical ointment, the calcium carbonate, magnesium hydroxide and aluminum hydroxide may first be mixed with water, with the water being added a little bit at a time to form a smooth moist mixture having a paste-like consistency and which contains approximately 37 weight percent calcium carbonate, 29.7 weight percent magnesium hydroxide and 33.3 weight percent aluminum hydroxide. The paste thus formed containing the non-systemic basic materials may then be added to a homogenous mixture of anhydrous lanolin, hydrophlic ointment, vitamin A, and zinc chloride with continuous mixing to insure homogenity and provide a pH of from about 6.5 to 7.5. The composition thus prepared has a weight ratio of carrier material to non-systemic basic materials of about 84:1.

When the composition is applied topically, it is believed that the calcium carbonate and the magnesium hydroxide provide a rapid neutralization of the area under treatment, while the aluminum hydroxide provides a slower but longer lasting neutralization, and in addition, a mild astringent effect. The anhydrous lanolin and the hydrophilic ointment provide a carrier base which facilitates application of the composition as a semi-solid homogeneous paste, and enhances lubrication and adsorption by the skin.

Aluminum hydroxide, mol. wt. 77.9, is a white, bulky amorphous powder that is practically insoluble in water, but soluble in alkaline aqueous solutions or in HCl, $H_2SO_4$ and other strong acids in the presence of water. It forms a gel on prolonged contact with water and absorbs acid gases such as $CO_2$. Aluminum hydroxide provides a mild astringent and demulcent action which produces healing effect on irritated and ulcerated mucosa. Moreover, this compound is non-toxic because it is not absorbed.

Calcium carbonate, mol. wt. 100.09, is odorless and tasteless and may exist as a powder or a crystalline form. It is practically insoluble in water, but soluble in dilute acids.

Magnesium hydroxide, mol. wt. 58.34, is an amorphous powder, practically insoluble in water (1:80,000), but soluble in dilute acids. It imparts slight alkaline reaction properties to water, the pH of aqueous slurry generally being in the range of from 9.5 to 10.5, and it absorbs $CO_2$ in the presence of water.

Anhydrous lanolin is chemically a wax rather than a fat, being a complex mixture of esters and polyesters of 33 high-molecular-weight alcohols and 36 fatty acids. The alcohols are generally of three types: aliphatic, steroid, and triterpenoid. The acids are also generally of three different types: saturated non-hydroxylated acids, unsaturated non-hydroxylated acids; and hydroxylated acids. It is a yellowish, tenacious, semi-solid fatty material having a slight odor or being practically odorless. Its melting point is 38°–42° C. and it is practically insoluble in, but mixes with twice its weight of water without separation. Anhydrous lanolin is sparingly soluble in cold alcohol, more soluble in hot alcohol and freely soluble in benzene, chloroform, ether, carbon disulfide, acetone and petrol ether.

Hydrophilic ointment consists of a mixture of approx. 25 parts by weight (pbw) white soft paraffin, approx. 25 pbw stearyl alcohol, approx. 12 pbw propylene glycol, approx. 1 pbw sodium lauryl sulfate, approx. 25 pbw methylhydroxybenzoate, approx. 15 pbw propylhydroxybenzoate, and approx. 37 pbw water. It is insoluble in water, acetone and alcohol, soluble in benzene, carbon disulfide, chloroform, ether, light petroleum and fixed and volatile oils. the solutions sometimes show a slight opalescence.

The foregoing components are described in more detail in said prior patent U.S. Pat. No. 4,005,191.

The zinc component, which may preferably be included in the form of zinc chloride, may be present in the ointment in a proportion ranging from 0.05 mg to about 50 mg in the form of the invention set forth above, and generally may be present in the composition in the range of from about 0.15 to about 15 weight percent based on the total amount of the non-systemic basic materials in the composition. The zinc may also be present in the form of other physiologically acceptable salts such as, for example, the acetate, citrate, sulfate, perioxidase or salicylate. Zinc is a stably-bound constituent of at least 25 enzymes involved in digestion and metabolism. Insulin forms complexes with zinc which permit crystalline zinc insulin to be prepared during insulin purification. Zinc is important in wound healing and zinc chloride is a known escharotic and fungicidal agent. Zinc and vitamin A are synergistic in the presence of one other. It is also known that zinc ions are capable of forming chelates with fully ionized amino acids which have given up a hydrogen ion at each of their carboxyl and amino groups.

Vitamin A may be included in the ointment composition as an antioxidant. The proportional amount of vitamin A may vary from 5 International Units (IU) to 500,000 IU; and preferably ranges between 100 IU and 20,000 IU. Vitamin E may also be added to the composition in a proportional amount of from about 2 IU to about 1600 IU and preferably in a proportional amount of between 2 IU and 800 IU. Vitamin E will, when used, enhance the antioxidant effect of vitamin A and when using both vitamins, each may be included in a lower amount than when one alone is used.

In accordance with the present invention, it has been found that the rate of development of dermatitis, as characterized by inflammation, blanching, discoloration, and complete invasion of the dermis, epidermis and subcutaneous tissue as is sometimes found in long-term care institutions, may be substantially retarded by daily application of both a pretreament moisturizing composition and the ointment composition described above. Moreover, the rate of healing of epidermal wounds and the like and particularly of decubitus ulcers may be substantially enhanced by this new procedure.

The topical ointment acts as a protestant and is a pH balanced ointment with antibacterial, adsorbent, astringent properties. The ointment affords relief for a variety of skin conditions such as friction burns, minor burns, sunburn, lacerations, abrasions, chaffing, peeling and scaling lesions. The ointment is effective for neutralizing acids and other toxins in gangrene and may be used as a skin protectant for areas prone to friction and pressure, urine scalds and jock rash. The ointment protects the skin around tracheostomy and ostomy sites and acts to relieve itching, irritation and discomfort of moist rectal conditions.

In accordance with the invention, a moisturizer composition useful for pretreating wounds in human skin may comprise an aqueous solution containing a water-soluble zinc salt in an amount physiologically effective to enhance wound healing. The composition may also contain a physiologically active amount of a vitamin $B_6$ compound effective upon application to an open wound area to stabilize and precondition the open wound and create therein a physiological environment conducive of healing of the wound.

The aqueous moisturizer composition may contain pyridoxine hydrochloride as the vitamin $B_6$ component and zinc chloride, each in concentrations of about 3% by wt in an isotonic solution of dextrose, NaCl, water and ethanol. Other zinc salts that may be used to replace all or part of the zinc chloride include the acetate, salicylate, sulfate, citrate and perioxidase salts, and in general, any water-soluble, pharmaceutically acceptable zinc salt is suitable. The pretreatment composition operates to stabilize the wound and it is believed that with appropriately adjusted pH levels, the composition will cause migration of tissue building blocks, such as amino acids, to the wound site.

While it is preferred to include dextrose as the sole source of carbohydrates, such source may also include glycerol or another dermatologically acceptable material compatible with dextrose, such as ethanol and/or propylene glycol.

The pyridoxine HCl concentration may vary from 1 mg to 100 mg per 100 ml of solution and preferably will be in the range of 5 mg to 25 mg per 100 ml of solution.

The zinc salt concentration may generally vary from 0.05 mg to 50 mg per 100 ml of solution and preferably will be within the range of from about 0.15 to 15 mg per 100 ml of solution.

As with any new modality, the present invention has qualities compatible for other uses. The pretreatment moisturizer composition, for example, when used on pustular acne problems found in teenagers and young adults, has proven effective for cleansing the skin and also to promote healing to areas such as the face, neck and back. This composition has also been used to treat vaginal warts and venous stasis ulcers and to remove scales seen in many dermatological problems.

The moisturizing composition is a gentle skin protectant spray and may be used in the case of a variety of skin conditions as a protectant, antiseptic, anti-fungicide spray. The composition may be used to remove necrotic scaly debris on the surface of the skin and skin lesions and is effective as a gentle spray in cleansing and de-odorizing perineal areas exposed to human excreta. This composition may be used for protecting areas around stoma and tracheostomy sites and is useful in cleaning ostomy appliances. The composition affords relief for urine burns, sunburns, chapping, peeling and scaling conditions of the skin and is useful as a skin protectant in areas of oozing and/or weeping due to rubbing or friction.

In sum, the moisturizing and stabilizing composition may be a mixture of a vitamin $B_6$ compound and a zinc salt in a solution of dextrose, alcohol and sodium chloride. Phenyl mercuric nitrate N.F. may also be included as a stabilizer.

The topical ointment may include a mixture of zinc chloride, magnesium hydroxide, aluminum hydroxide and calcium carbonate. The ointment provides a non-systemic source of di-basic cations set in a fatty acid carrier base of anhydrous lanolin, hydrophilic ointment and vitamin A.

Indolent wound site environment is generally very unstable and, therefore, unpredictable as to pH, bacterial count and blood sugar levels. The basal areas of such wounds are usually acidotic with pH readings as low as 3. Bacterial counts usually show leukocytes, *E coli* and pseudomonas to be present. Blood sugar levels are usually low within the wound bed. Accordingly, it is the intent of the present invention to provide for stabilization of the wound site prior to application of a non-systemic basic ointment in the treatment of indolent wounds such as decubitus and venous stasis ulcer disease.

In a useful form, the moisturizing pretreatment composition may consist of:

| INGREDIENT | QUANTITY |
| --- | --- |
| pyridoxine hydrochloride U.S.P. | 25 mg |
| zinc chloride U.S.P. | 0.15 mg |
| dextrose U.S.P. | 5 gm |
| ethanol U.S.P. | 5 ml |
| sodium chloride U.S.P. | 0.9 gm |
| phenyl mercuric nitrate N.F. as a stabilizer | trace |
| distilled water | up to 100 ml |

The moisturizer comprises a formula which is believed to provide the critical cofactors needed for activating the metabolic pathways of wound areas and prepare the same to accept a topical treatment with an ointment containing magnesium hydroxide, aluminum hydroxide, calcium carbonate and zinc chloride in a fatty base carrier of anhydrous lanolin, hydrophilic ointment and vitamin A. In this regard it is believed that the moisturizer may act as a catalyst energizer to the ointment in the treatment of wound areas. The moisturizer in combination with the ointment may provide the correct balance of pH and natural excipients to enhance wound healing.

Vitamin $B_6$ is a complex of closely related compounds which are interconvertible and biologically active. The parent compound is pyridine, and either an alcohol (pyridoxine), aldehyde (pyridoxal), or amino (pyridoxamine) group is attached to the pyridine nucleus.

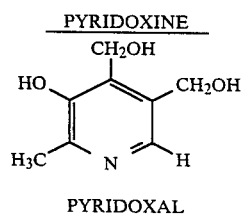

PYRIDOXAL

-continued

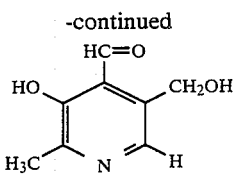

PYRIDOXAMINE

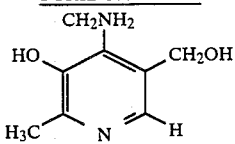

Vitamin B<sub>6</sub> compounds are generally metabolically active in their phosphorylated forms mainly as pyridoxal-5-phosphate (PLP). In this form, the vitamin functions as a coenzyme in several enzyme systems, most of which are concerned with protein and carbohydrate metabolism. As PLP, vitamin $B_6$ has been found to be an essential part of the enzyme glycogen phosphorylase, which is active to bring about the conversion of glucose to glucose 1-phosphate. The vitamin $B_6$ compound, as used in the invention, may be in any of the forms mentioned above and may also be in the form of live yeast derivative factors (LYDF) such as torula yeast or brewer's yeast.

Pyridoxal phosphate is also an essential co-factor for an important group of enzymes known as transaminases. These enzymes transfer amino groups from an amino acid to a keto acid. Measurements of transaminase activity in serum are frequently useful in clinical medicine as a measure of tissue injury or death, since the enzymes survive the breakdown of cells and then leak into the bloodstream.

Pyridoxal phosphate functions in transamination, deamination, decarboxylation, and racemization reactions.

PYRIDOXAL PHOSPHATE

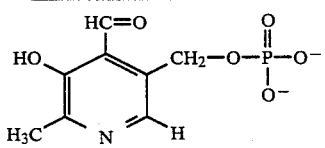

As has been set forth above, zinc is a stably bound constituent of at least 25 enzymes involved in metabolism. Insulin forms complexes with zinc whereby crystalline zinc insulin may be prepared during insulin purification. Zinc adhering to the insulin molecule increases the duration of insulin action. Carbonic anhydrase is a metalloenzyme in which one mole of zinc/mole of protein is needed for its activity. This chemical may be included in an amount which is physiologically effective to enhance wound healing.

Biochemical reactions generally occur in dilute aqueous solutions and accordingly, the concentration of water in the moisturizer does not change significantly and is initially set to unity. Water is used as a carrier in this composition.

Body fluids include intracellular and extracelluar fluids, the latter including interstitial fluids and circulatory fluids. Total body fluid constitutes 70% of lean body mass. The osmolarity of extracellular fluid fluctuates largely as a result of changes in concentration of NaCl and other ionic and non-ionic species. There is a continuous movement of Na<sup>+</sup> ions into the cells, and such movement is opposed by the active transport of the ions into extracellular space. This movement constitutes the active transport essential to life.

Some solutes are essentially compartmentalized in extracellular spaces although water is freely permeable. Accordingly, the volume of the extracellular spaces reflects their concentration of Na<sup>+</sup> ions.

Upon absorption of the moisturizing composition into the wound site, carbonic anhydrase activity is stimulated, resulting in increased availability of H<sup>+</sup> ions, an increase in reabsorption of HCO<sub>3</sub><sup>-</sup> and an increase in NH<sub>4</sub><sup>+</sup> excretion. The ethanol also acts as an astringent and an antiseptic.

Potassium is generally present in dying cells. When the moisturizer composition of the present invention is applied to the wound area, it is believed that the potassium is shifted back into the cell, and the Na-K pump is properly restarted.

The major function of the dextrose or other carbohydrates, in accordance with metabolic processes of the present invention, is as a fuel to be oxidized and provide energy. The simplest form of carbohydrates are simple sugars. Alcohols are also carbohydrates. The metabolism of carbohydrate may be subdivided into the following areas:

1. Glycolysis: The oxidation of glucose to pyruvate and lactate by the Embden-Myerhof Pathway.
2. Glycogenesis: The synthesis of glycogen from glucose.
3. Glycogenolysis: The breakdown of glycogen to glucose.
4. Oxidation of Pyruvate to Acetyl Co-A: A necessary step prior to entrance of end products of glycolysis into Krebs Cycle.
5. Hexose Monophosphate Shunt: Alternative pathway for the oxidation of glucose.
6. Gluconeogenesis: Formation of glucose or glycogen from noncarbohydrate sources.

Dextrose thus provides a rich store of potential energy which is converted with other components into complex organic substances such as other carbohydrate, protein and fat. It is the basis for the metabolism of most organisms. Dextrose is a pre-cursor for the building blocks used in cell formation.

WOUND-MUSCLE PROTEIN AMINO ACID GLYCINE

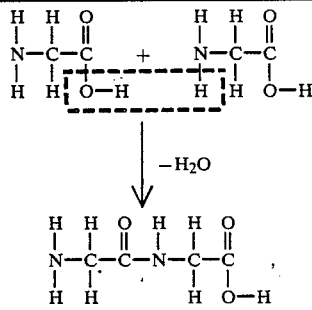

Varied combinations of amino acids available through biosynthesis make protein available for new granulation tissue to form.

Since completing the work which led to the filing of parent application Ser. No. 847,234, it has been discovered that the pH of the wound area is a very important factor in wound healing. As mentioned above, the untreated wound area is often very low in pH and in fact the pH levels at the wound surface are often so low that amino acid activity is inhibited and perhaps totally precluded. That is to say, the pH level at the surface of the wound is often so low that the amino acids necessary for healing to occur are kept in an unionized state and are thus prevented from entering into aqueous solution for transport to the surface of the wound.

In accordance with the present invention, it has been found that if the wound area is treated with an aqueous medium having a pH sufficiently high to cause, it is believed, at least partial ionization of the basic amino acids naturally present in tissues adjacent the wound area and bring such amino acids into solution at the surface of the wound area, healing activity may be enhanced. The healing is particularly enhanced, if after the amino acids are ionized and brought to the surface of the wound area, the latter is treated with a basic ointment material having a pH level sufficient for activating basic amino acids such as lysine. Such activation may be the result of full ionization of both the carboxyl and amino groups of the acid and the provision of a chelation agent to tie the amino acid up and maintain it in an activated state.

It is believed that in particular the basic amino acids, and specifically lysine, are needed in the wound healing process. Accordingly, as a first step in accordance with the invention, the pH of the aqueous medium should be above 4.25 and particularly should be high enough to cause at least partial ionization of lysine. In accordance with the present invention, it has been determined that the pH of the aqueous medium should preferably be in the range of from about 4.3 to 6.8 and even more usefully should be in the narrow range of from about 5.5 to 5.8. It has also been discovered, in accordance with the present invention, that the aqueous medium should preferably contain a chelating agent for amino acids, and it is theorized that the presence of the chelating agent assists in the mechanism for causing the amino acids, and particularly the basic amino acids, to migrate to the surface of the wound site. Manifestly, it is believed that the presence of the amino acids in ionized form at the surface of the wound area will also cause corresponding migration of ions of the chelating materials toward the wound bed.

While ionized amino acids and the ions of the chelating agent are present adjacent the surface of the wound area, the pH of the wound bed, in accordance with the present invention, is then adjusted to a pH which is sufficiently high to activate the amino acids and particularly the basic amino acids at the surface of the wound. Thus, the amino acid ions and the chelate agent ions are able to form a chelate. In this regard, the activation process is believed to involve the ionization of the amino groups to thus provide two active sites for linking with the chelate ion.

The activation process takes place as a result of the application of the basic ointment to the wound area. The ointment should have a pH in the range of from about 6.5 to about 9.0 to effect the activation. The ointment is simply applied to the previously moistened wound area and the pH then at the boundry between the ointment and the wound area is sufficient to cause ionization of the amino groups of the amino acids and permit the amino acids to form chelates with bivalent chelating agent ions. The chelates then are free to migrate and participate in the wound healing process.

Pursuant to the present invention, it has been found that the pH levels of the moisturizing medium and the ointment should be such that the median thereof is approximately the same as the normal pH of the tissue undergoing treatment. That is to say, epidermal tissues naturally and normally have a pH level in the range of about 6.0 to 6.1 and thus the pH levels of the moisturizing medium and of the ointment should be selected such that the median thereof is about 6.0 or so. This can be accomplished, for example, by using a moisturizing medium having a pH of about 5.5 and an ointment wherein the pH has been adjusted to about 6.5. The adjustments of the pH in each instance may be accomplished simply by adjusting the amount of zinc chloride or other chelating agent in each of the materials.

On the other hand, for treatment of internal, that is dermal tissues, which have a normal pH in the range of about 7.0, it has been found desirable to employ a moisturizing medium and an ointment having respective pH levels such that the median is about 7.0. This can be accomplished, for example, by utilizing a moisturizing medium having a pH of about 5.5 and a basic ointment having a pH level of about 8.5.

In accordance with the invention, the moisturizing medium may preferably have the following composition:

| INGREDIENTS | CONCENTRATION |
|---|---|
| corn syrup | 5% |
| SDA alcohol 40-2 (denatured ethanol) | 5% |
| sodium chloride U.S.P. | 0.9% |
| pyridoxine hydrochloride | 25 mg/30 ml |
| zinc chloride U.S.P. | 0.15 mg/30 ml |
| phenylmercuric nitrate, N.F. | 0.01% |
| deionized water U.S.P. | Q.S. 100% |

This formulation, it has been found, has a pH of about 5.5, and of course, as set forth above, if necessary the pH can be adjusted by manipulating the zinc chloride content.

In the preferred form of the basic ointment, the same may have the following formulation:

| INGREDIENT | QUANTITY |
|---|---|
| zinc chloride | 0.001 gm |
| magnesium hydroxide | 0.275 gm |
| aluminum hydroxide | 0.250 gm |
| calcium carbonate | 0.150 gm |
| sodium chloride | 0.025 gm |
| vitamin A | 5000 IU |
| hydrophilic ointment | 13.761 gm |
| anhydrous lanolin | 13.761 gm |
| deionized water | 0.127 gm |
| TOTAL | 28.35 gm |

The foregoing formulation provides one ounce of an ointment having a pH of approximately 8.5. This ointment may be utilized in conjunction with the moisturizing medium described above for treatment of dermal tissue since the median of the pH levels of the ointment and the medium is 7.0.

The pH of the ointment may be manipulated by changing the concentration of the zinc chloride component and correspondingly adjusting the amounts of hydrophilic ointment and anhydrous lanolin. For example, to achieve a pH of about 6.5, the zinc chloride content in the about formulation may be increased to 0.008 gm and the quantities of hydrophobic ointment and anhydrous lanolin may be adjusted respectively downwardly to 13.7025 gm each.

In sum, it is the objective of the invention to first adjust the pH of the wound situs to a level conducive to the migration and/or presence of amino acids, and in particular basic amino acids, into solution at the surface of the wound area. Thereafter, the invention provides means for activating the amino acids by providing an increased pH. It is believed that the activation occurs as a result of the ionization of both the acid and amino groups of the amino acid and the availability of a chelation agent, whereby the amino acid and the chelation agent may migrate together to participate fully in the wound healing mechanism.

In accordance with the invention, the amino acids and other tissue building blocks, as well as the zinc or other chelating agent, are in solution at the surface of the wound as a result of the application of the moisturizing medium to the wound site. The basic ointment is then applied and this will effectively prevent hydrogen ion interference with the chelation process. In this way, natural processes are simulated, and in this regard it is important that the present invention permits usage of amino acids, polypetides and other building blocks which were created by natural hydrolyzation of naturally occurring proteins. The wound bed itself is thus the source of the amino acids, etc.

The preferred procedure for treatment of wounds in accordance with the invention is as follows:

1. Irrigate the wound area with the aqueous moisturizing medium;
2. Impregnate a gauze strip with the non-systemic basic ointment and utilize this to pack the wound—a thin layer will suffice;
3. Dress the wound and repeat the procedure each 8 hours.

In the foregoing disclosure, although zinc is described as the preferred chelating agent, it should be noted that other chelating agents might be used as well. In this regard, calcium and magnesium should be capable of forming at least weak chelates with amino acids, and the transition metals such as vanadium, molybdenum, chromium, manganese, iron, cobalt and copper should be capable of forming strong chelates with amino acids. Accordingly, it should be possible to use ionizable salts of these metals in place of and for the same essential purposes as the zinc salts disclosed herein.

I claim:

1. A method for treating open wounds in mammalian tissue comprising:
    treating the wound area with an aqueous medium having an acidic pH sufficiently high to cause at least partial ionization of basic amino acids naturally present in tissues adjacent the wound area and bring such amino acid into aqueous solution at the surface of the wound area; and thereafter
    applying to the treated wound area a basic ointment material comprising a non-systemic basic material and having an alkaline pH level sufficient for activating basic amino acids at the surface of the wound.

2. A method as set forth in claim 1, wherein the pH of said medium is in the range of from about 4.3 to 6.8.

3. A method as set forth in claim 2, wherein the pH of the medium is about 5.5 to 5.8.

4. A method as set forth in claim 3, wherein said medium contains zinc and chloride ions.

5. A method as set forth in claim 1, wherein said aqueous medium contains a chelating agent for activated basic amino acids.

6. A method as set forth in claim 5, wherein said chelating agent comprises zinc ions.

7. A method as set forth in claim 1, whereas the pH of said ointment material is in the range of from about 6.5 to 9.0.

8. A method as set forth in claim 7, wherein the pH of the ointment is about 8.5.

9. A method as set forth in claim 1, wherein said ointment material comprises magnesium hydroxide 10. A method as set forth in claim 9, wherein said ointment material comprises a mixture of magnesium hydroxide, aluminum hydroxide and calcium carbonate.

11. A method as set forth in claim 1, wherein said ointment comprises an ionizable zinc salt and the pH of the ointment is manipulated to achieve the desired level by adjusting the concentration of the zinc salt in the ointment.

12. A method as set forth in claim 1, wherein the respective pH levels of the aqueous medium and the ointment are selected such that the normal pH of healthy tissue of the type being treated is approximately at the median of such levels.

13. A method of treating open wounds in human tissue comprising:
    treating the wound area with an aqueous medium containing a chelating agent for activated amino acids and having a pH in the range of from about 4.3 to 6.8; and thereafter,
    applying, to the treated wound area, an ointment material containing a non-systemic basic material and having a pH in the range of from about 6.5 to 9.0,
    the pH levels of the medium and the ointment being such that the normal pH of healthy tissue of the type being treated is approximately at the median of such levels.

14. A method for treating open wounds in human dermal tissue comprising:
    treating the wound area with an aqueous medium containing a chelating agent for activated amino acids and having a pH in the range of from about 4.3 to 6.8; and thereafter,
    applying, to the treated wound area, an ointment material containing a non-systemic basic material and having a pH in the range of from about 7.0 to 9.0,
    the pH levels of the medium and the ointment being selected such that the median of such levels is in the range of approximately 6.75 to 7.45.

15. A method as set forth in claim 14, wherein said median is approximately 7.0.

16. A method for treating open wounds in human epidermal tissue comprising:
    treating the wound area with an aqueous medium containing a chelating agent for activated amino acids and having a pH in the range of from about 4.3 to 6.8; and thereafter,
    applying, to the treated wound area, an ointment material containing a non-systemic basic material and having a pH in the range of from about 6.5 to 9.0, the pH levels of the medium and the ointment being selected such that the median of such levels is in the range of approximately 6.0 to 6.4.

17. A method as set forth in claim 16, wherein said median is approximately 6.1.

18. A method for treating open wounds in mammalian tissue comprising:
stabilizing the wound area by moistening the same and adjusting the pH thereof to an acidic level sufficient for causing naturally occurring basic amino acids to be present in aqueous solution at the surface of the wound area; and thereafter,
applying an ointment containing a non-systemic basic component to the stabilized wound area, said ointment having an alkaline pH level sufficient to activate basic amino acids.

19. A method as set forth in claim 18, wherein said stabilization includes providing a chelating agent for activated basic amino acids at said surface of the wound area.

20. A method as set forth in claim 19, wherein said stabilizing includes stimulating the carbonic anhydrase activity of the wound area.

21. A method as set forth in claim 19, wherein said stabilizing includes applying a physiologically effective amount of a vitamin $B_6$ compound to said wound area.

22. A method as set forth in claims 19, 20 or 21, wherein said stabilizing includes providing a carbohydrate fuel to the wound area.

23. A procedure for treating open wounds in mammalian tissue comprising:
stabilizing and preconditioning such wound by applying thereto a moisturizing quantity of an aqueous medium having an acidic pH sufficiently high to cause at least partial ionization of basic amino acids naturally present in tissues adjacent the wound area and bring such amino acids into aqueous solution at the surface of the wound area, said medium comprising an active amount of a chelating agent for activated basic amino acids in a water carrier; and thereafter,
covering the stabilized wound area with a topical ointment comprising magnesium hydroxide in an amount effective to promote growth of normal healthy body tissue, and a carrier therefor comprising anhydrous lanolin and a hydrophilic ointment, said ointment having a pH in the range of from about 6.5 to 9.0 effective for activating basic amino acids at said surface.

24. A procedure as set forth in claim 23, wherein said chelating agent includes a water-soluble zinc salt present in the medium in the amount physiologically effective to enhance wound healing.

25. A procedure as set forth in claims 23 or 24, wherein said medium includes an amount of carbohydrate physiologically effective to provide tissue building fuel to the open wound area.

26. A procedure as set forth in claims 23 or 24, wherein said topical ointment includes a water-soluble zinc salt in an amount physiologically effective to enhance wound healing.

27. A procedure as set forth in claims 23 or 24, wherein said medium includes an amount of a carbohydrate physiologically effective to provide tissue building fuel to the open wound area and said topical ointment includes a waste-soluble zinc salt in an amount physiologically effective to enhance wound healing.

28. A liquid composition for treating open wounds in human skin tissue comprising an aqueous solution containing a chelating agent for activated amino acids and having a pH in the range of from about 4.3 to 6.8 effective upon application to such wound area to moisturize, stabilize and precondition the open wound and create at the surface thereof an aqueous physiological environment conducive to healing of the wound and containing at least partially ionized basic amino acids.

29. A composition as set forth in claim 28, wherein said chelating agent comprises a water-soluble zinc salt, said salt being present in the solution in an amount physiologically effective to enhance wound healing.

30. A composition as set forth in claim 28, wherein said zinc salt is selected from the group consisting of zinc chloride, zinc sulfate, zinc perioxidase, zinc citrate, zinc acetate and zinc salicylate.

31. A composition as set forth in claim 28, wherein said solution contains a physiologically active amount of vitamin $B_6$ compound.

32. A composition as set forth in claim 31, wherein said chelating agent comprises a water-soluble zinc salt, said salt being present in the solution in an amount physiologically effective to enhance wound healing.

33. A composition as set forth in claim 32, wherein said zinc salt is zinc chloride and said vitamin $B_6$ compound is pyridoxine HCl.

34. A composition as set forth in claim 33, wherein is included an amount of dextrose physiologically effective to provide nutrients to and enhance healing of the wound.

35. A topical ointment composition comprising an admixture of a non-systemic basic material, anhydrous lanolin, hydrophilic ointment and a water-soluble zinc salt;
said basic material including calcium carbonate, magnesium hydroxide and aluminum hydroxide in amounts effective for promoting growth of normal healthy body tissues;
said zinc being present in an amount physiologically effective to enhance wound healing and provide a pH level in the ointment in the range of about 6.5 to 9.0,
said anhydrous lanolin and said hydrophilic ointment being present in amounts effective for carrying the other ingredients, facilitating application of the other ingredients to the wound area and maintaining the other ingredients in wound healing proximity to the wound.

36. An ointment composition as set forth in claim 35, wherein is included an amount of vitamin A effective to act as an anti-oxidant for the compostiion.

37. An ointment composition as set forth in claims 35 or 36, wherein the zinc salt is included in an amount ranging from about 0.15 to 15 weight percent of the total non-systemic basic material in the composition.

38. An ointment composition as set forth in claim 37, wherein said zinc salt is selected from the group consisting of zinc chloride, zinc sulfate, zinc perioxidase, zinc citrate, zinc acetate and zinc salicylate.

* * * * *

UNITED STATES PATENT AND TRADEMARK OFFICE
CERTIFICATE OF CORRECTION

PATENT NO. : 4,847,083
DATED : July 11, 1989
INVENTOR(S) : Mary G. Clark

It is certified that error appears in the above-identified patent and that said Letters Patent is hereby corrected as shown below:

Column 9, line 3, "protestant" should be --protectant--.

Column 15, line 1, "hydrophobic" should be --hydrophilic--.

Signed and Sealed this

Eighth Day of May, 1990

*Attest:*

HARRY F. MANBECK, JR.

*Attesting Officer*     *Commissioner of Patents and Trademarks*